US00PP10734P

United States Patent [19]

Wain

[11] Patent Number: Plant 10,734

[45] Date of Patent: Dec. 22, 1998

[54] CHRYSANTHEMUM PLANT NAMED 'WHITE GIANT TIME'

[75] Inventor: Peter Wain, Hapshire, United Kingdom

[73] Assignee: Cleangro, Ltd., West Sussex, England

[21] Appl. No.: 838,350

[22] Filed: Apr. 8, 1997

[51] Int. Cl.[6] ..... A01H 5/00

[52] U.S. Cl. ..... Plt./77

[58] Field of Search ..... Plt./77, 76

*Primary Examiner*—Howard J. Locker

*Attorney, Agent, or Firm*—Christie, Parker & Hale, LLP

[57] ABSTRACT

A new variety of Chrysanthemum plant having white flowers with pale yellow centers.

2 Drawing Sheets

BACKGROUND OF THE INVENTION

The present invention is directed to a new and distinct variety of Chrysanthemum botanically classified as *Dendranthema grandiflora*. The varietal denomination of the new Chrysanthemum is 'White Giant Time.'

The female and male parents of the new variety are unpatented, undistributed seedlings identified as P60-92 and P81-14, respectively. The new variety has been asexually reproduced by vegetative cuttings in Ventura County, Calif. and the distinguishing characteristics are retained through successive generations of asexual reproduction.

SUMMARY OF THE INVENTION

'White Giant Time' is a spray type pot forcing Chrysanthemum plant variety producing white flowers with pale yellow centers, and capable of being grown commercially in a greenhouse.

Comparision With 'Powerhouse'

BRIEF DESCRIPTION OF ILLUSTRATIONS

The accompanying photographs show typical specimens of the new variety with colors being as nearly true as possible with illustrations of this type. One illustration shows 'White Giant Time' grown as a pinched pot mum and the other illustration is a close-up of the flowers. The plant in the photograph, and described herein, is a spray type potted chrysanthemum. 'White Giant Time' can be commercially produced as either a spray type plant or disbud plant.

Description Of The Plant

The following description of the new variety is of specimens grown in a greenhouse in Ventura County, Calif. in the month of October. 'White Giant Time' has not been observed under all possible environmental conditions. The phenotype may vary significantly with variations in the environment such as temperature, light intensity, day length and cultural conditions. Color values provided in the description are from The Royal Horticultural Society Colour Charts (R.H.S.C.C.), unless otherwise indicated.

Plants of the new variety have been grown successfully under temperature conditions averaging about 65° F. at night and about 75°–85° F. during the day under light conditions of about 5,000–6,000 foot candles. The plants respond well to use of growth retardant, such as one B9 treatment at about 2000 ppm and one B9 treatment at about 1000 ppm. To produce a commercial product the plants may be pinched twice with the center bud removed. It has been observed that the shelf life of 'White Giant Time' is about 18 days with the response time of about 9 weeks.

Plant

Habit: Branching, and upright.

Height: About 21 cm after growth regulated treatment described above.

Branching characteristics: Good branching from pinches.

Number of breaks from pinch: About 3 to 4.

Typical container size to be grown in: 4", 6", 8", 10".

Length of lateral branches: Average—about 16.5 cm from second pinch.

Stem color: Near 138B, Tomentose.

Foliage

Leaf arrangement: Alternate.

Number of leaves per lateral branch: Average per lateral branch—about 10 all stages, not extremely leafy.

(1) *Size*.—Length — Average about 9.5 cm; Width — Average about 5.2 cm.

(2) *Shape*.—Ovate.

(3) *Attachment*.—Petioled.

(4) *Apex*.—Acuminate.

(5) *Base*.—Tapered.

| (6) | Color: | Mature | Young |
|---|---|---|---|
| | Top: | Near 147A | Near 137A |
| | Bottom: | Near 137D | Near 138B |

Margin: Lobed, dentate.

Aspect: Slight undulation.

Surface characteristics: Top—puberulent; Bottom—puberulent.

Venation: Net, with prominent mid vein. Veins are prominent on underside of leaf. Main vein coloration near 144D.

Petiole:

(1) *Length*.—About 2.25 cm.

(2) *Color*.—Near 144D (3) *Other Characteristics*.—Slightly winged, tomentose

Stipule: Rarely present, 1 or 2 per leaf when present, small, spiky.

FLOWER

Inflorescence form: Cymose cluster.

Flower form: Decorative.

Flower shape: Flattened.

Flower color (general): White with pale yellow centers, center flower color near 13D.

Blooms: About 10 blooms per branch from first pinch.

(1) *Diameter*.—About l0 cm.

(2) *Depth*.—About 2 cm.

Sepal:

(1) *Number*.—About 35.

(2) *Color*.—Near 137B.

(3) *General appearance*.—Highly membranous inner sepals, first outer set very tough. Outermost ring of sepals are thick and fleshy, inner rings of sepals are paper thin.

Peduncle:

(1) *Length*.—Average about l0cm.

(2) *Habit*.—Upright, sturdy and straight.

(3) *Surface*.—Tomentose.

(4) *Color*.—Near 147C.

(5) *Strenqth*.—Very sturdy.

Bud:

(1) *Shape*.—Flattened sphere.

(2) *Diameter*.—Avg. about 0.9 cm.

(3) *Color*.—Near 137 C.

(4) *Height*.—About 0.6 cm.

Ray florets:

(1) *Number per inflorescence*.—About 240.

(2) *Fused*.—No.

(3) *Texture*.—Matte.

(4) *Shape*.—Elliptic.

(5) *Apex*.—3-lobed, middle longer than sides.

(6) *Base*.—Tapered.

(7) *Margin*.—Entire.

(8) *Aspect*.—Undulating.

(9) *Length*.—Avg. About 4.8 cm.

(10) *Width*.—Avg. About 1.5 cm.

*Color — top side*.—Immature: Near 11D. Mature: Near 155D. Fading: Near 155D.

*Color — under side*.—Immature: Near 11D. Mature: Near 155D. Fading: Near 155D.

Disc florets:

(1) *Number per inflorescence*.—Average about 50.

(2) *Texture*.—Glossy, ridged.

(3) *Shape*.—Cylindrical.

(4) *Margin*.—Entire.

(5) *Length*.—About 0.3cm.

(6) *Width*.—About 0.1cm.

(7) *Fragrance*.—Almost none, light musky.

*Color*.—Immature: Near 2B. Mature: Near 16A. Fading: Near 17D.

Description of flower as it ages: Flower shape becomes very spherical and petals very loose. Center turns brown.

Reproductive Organs

Ray Florets:

*Pistillate*.—(1) Pistil number: 1 per floret. (2) Receptacle shape: Sphere with domed top. (3) Stigma shape: Forked and curving broadly out. (4) Stigma color: Near 5A. (5) Style length: About 0.35 cm. (6) Style color: Near 154D.

Disc Florets: Both staminate and pistillate.

*Pistillate*.—(1) Pistil number: 1 per floret. (2) Stigma shape: Linear, near 154D. (3) Style length: About 0.25 cm, translucent.

*Staminate*.—(1) Stamen number: About 5. (2) Anther length: About 0.2 cm, near 15A. (3) Anther shape: Linear. (4) Pollen color: Near 15A. (5) Pollen quantity: Very little.

What is claimed is:

1. A new and distinct variety of Chrysanthemum plant as herein shown and described.

* * * * *

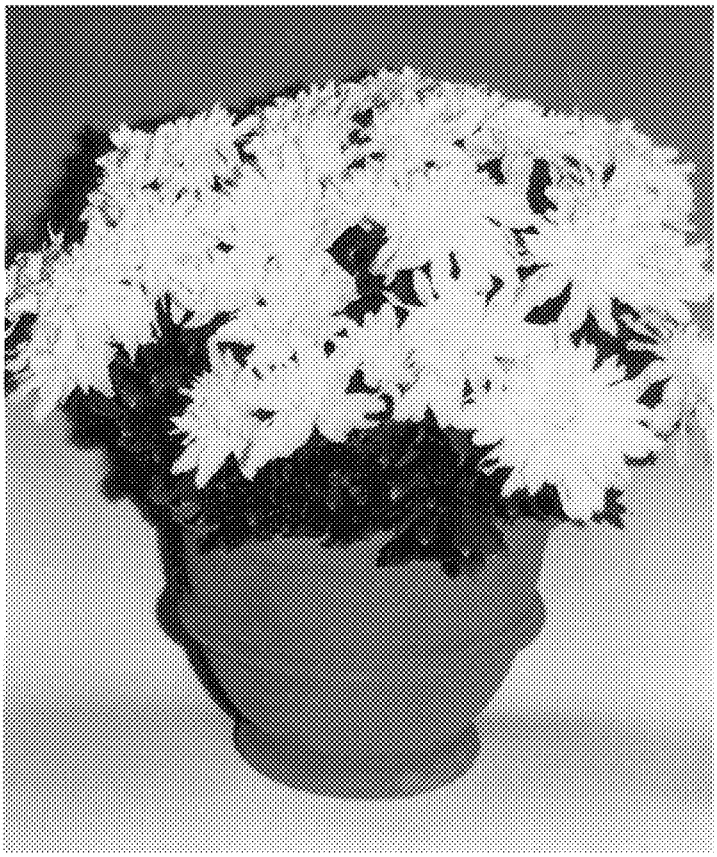

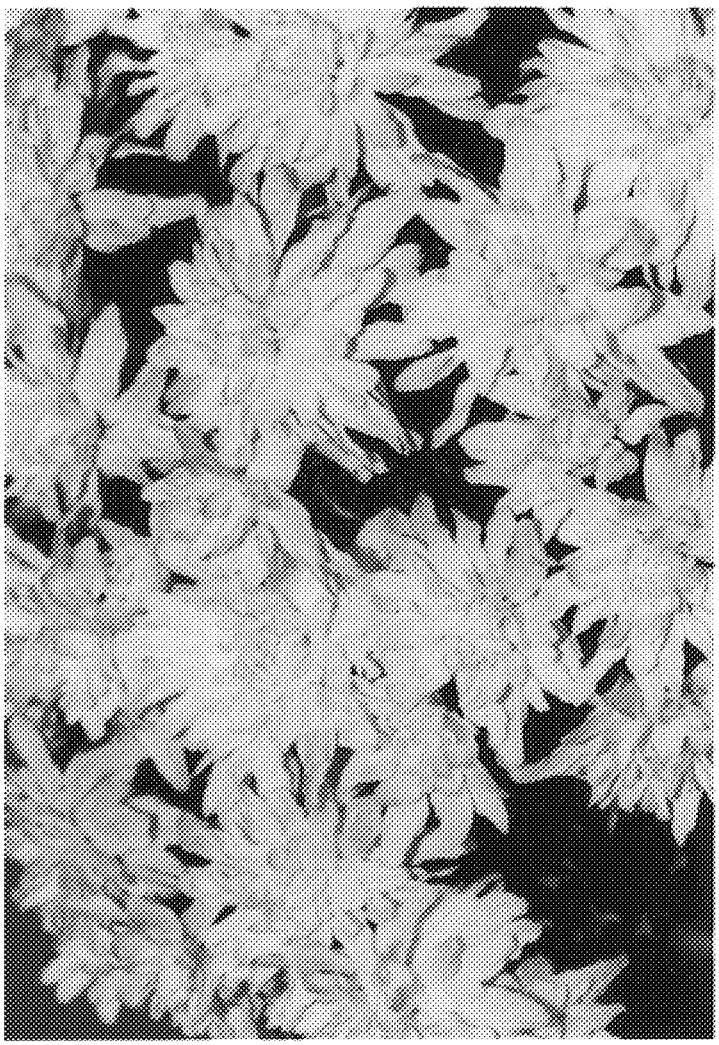

UNITED STATES PATENT AND TRADEMARK OFFICE

CERTIFICATE OF CORRECTION

PATENT NO. : Plant 10,734
DATED : December 22, 1998
INVENTOR(S) : Peter Wain

It is certified that error appears in the above-identified patent and that said Letters Patent is hereby corrected as shown below:

Column 3, line 18, replace "Strenqth." with -- Strength. --.

Signed and Sealed this

Twenty-eighth Day of March, 2000

*Attest:*

Q. TODD DICKINSON

*Attesting Officer*

*Commissioner of Patents and Trademarks*